US011839395B2

(12) United States Patent
Baril et al.

(10) Patent No.: US 11,839,395 B2
(45) Date of Patent: Dec. 12, 2023

(54) THREE-PRONG LAPAROSCOPIC GRASPING DEVICE

(71) Applicant: Covidien LP, Mansfield, MA (US)

(72) Inventors: Jacob C. Baril, Norwalk, CT (US); Nicolette R. LaPierre, Windsor Locks, CT (US); Roy J. Pilletere, Middletown, CT (US); Matthew A. Dinino, Newington, CT (US); Justin Thomas, New Haven, CT (US); Garrett P. Ebersole, Hamden, CT (US)

(73) Assignee: Covidien LP, Mansfield, MA (US)

( * ) Notice: Subject to any disclaimer, the term of this patent is extended or adjusted under 35 U.S.C. 154(b) by 91 days.

(21) Appl. No.: 17/324,281

(22) Filed: May 19, 2021

(65) Prior Publication Data

US 2021/0361310 A1    Nov. 25, 2021

Related U.S. Application Data

(60) Provisional application No. 63/026,996, filed on May 19, 2020.

(51) Int. Cl.
*A61B 17/29* (2006.01)
*A61B 17/30* (2006.01)

(52) U.S. Cl.
CPC ...... *A61B 17/29* (2013.01); *A61B 2017/2925* (2013.01); *A61B 2017/2938* (2013.01); *A61B 2017/301* (2013.01)

(58) Field of Classification Search
CPC ...... A61B 2017/303; A61B 2017/2925; A61B 2017/301; A61B 17/22031; A61B 17/30; A61B 17/44; A61B 17/29; A61B 10/06
See application file for complete search history.

(56) References Cited

U.S. PATENT DOCUMENTS

| | | | | |
|---|---|---|---|---|
| 5,281,220 A | * | 1/1994 | Blake, III | A61B 17/29 606/174 |
| 5,456,684 A | * | 10/1995 | Schmidt | A61M 1/772 606/174 |
| 5,704,925 A | | 1/1998 | Otten et al. | |
| 5,776,075 A | | 7/1998 | Palmer | |

(Continued)

FOREIGN PATENT DOCUMENTS

DE    4115136 A1    11/1992

*Primary Examiner* — Shaun L David
*Assistant Examiner* — Rachael L Geiger
(74) *Attorney, Agent, or Firm* — Carter, DeLuca & Farrell LLP

(57) ABSTRACT

A three-prong grasper for laparoscopic procedures includes an elongate body having a sleeve with a distal portion, and an end effector supported on the distal portion. The end effector includes a first prong assembly with a first base member and a first prong member pivotally secured to the first base member, a second prong assembly with a second base member and a second prong member pivotally secured to the second base member, and a third prong assembly with a third base member and a third prong member pivotally secured to the third base member. The first, second, and third prong members move between an open configuration and a closed configuration. A method of grasping tissue also includes pivoting first, second, and/or third prong members relative to respective first, second, and third base members to cause the grasping of tissue.

10 Claims, 8 Drawing Sheets

(56) References Cited

U.S. PATENT DOCUMENTS

| | | | |
|---|---|---|---|
| 5,910,144 A | 6/1999 | Hayashi | |
| 5,976,161 A * | 11/1999 | Kirsch | A61B 17/11 606/205 |
| 5,993,461 A | 11/1999 | Abae | |
| 6,989,020 B2 | 1/2006 | Jones et al. | |
| 2009/0030424 A1 | 1/2009 | Tuli et al. | |
| 2011/0276041 A1 * | 11/2011 | Nobis | A61B 17/29 606/1 |
| 2019/0150968 A1 * | 5/2019 | Winstanley | A61B 17/00234 |

* cited by examiner

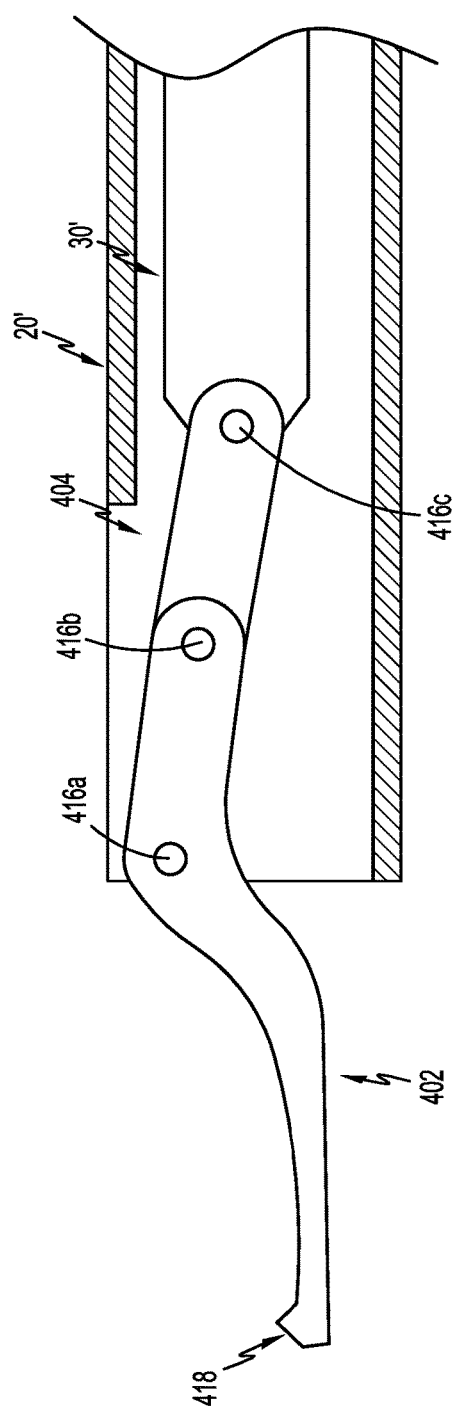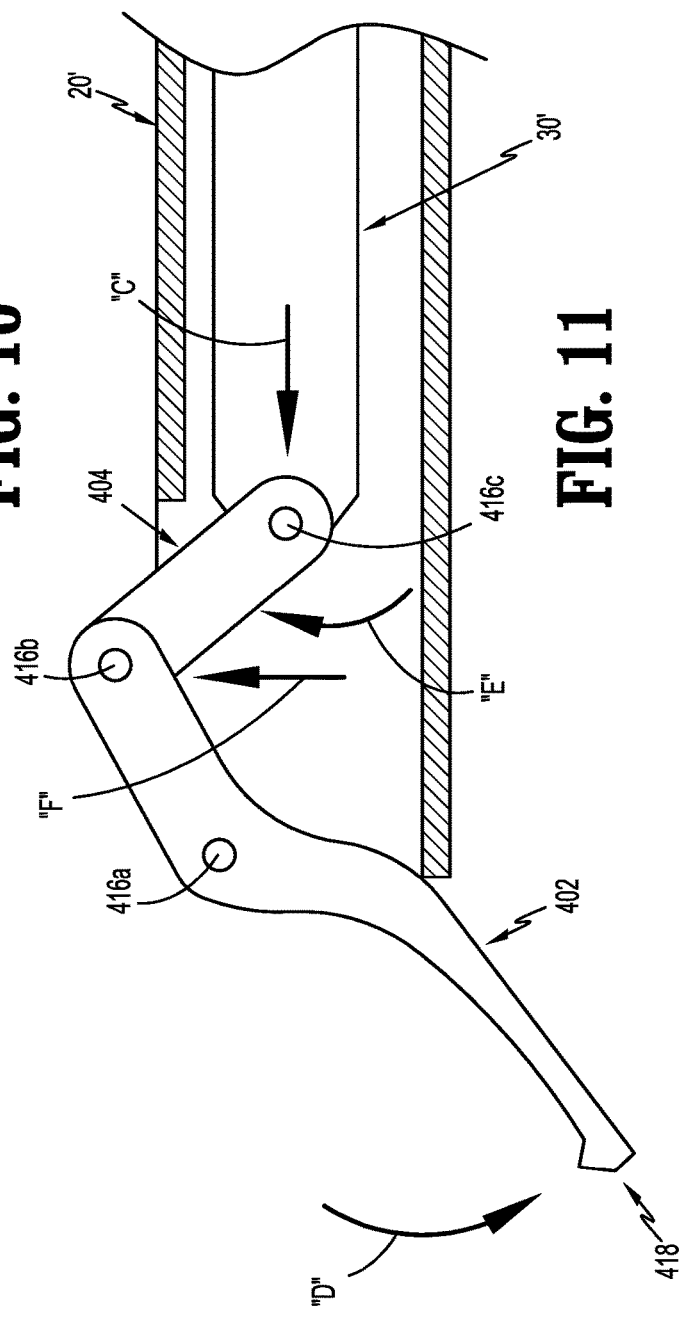

THREE-PRONG LAPAROSCOPIC GRASPING DEVICE

CROSS-REFERENCE TO RELATED APPLICATIONS

The present application claims the benefit of and priority to U.S. Provisional Patent Application Ser. No. 63/026,996, filed on May 19, 2020, the entire content of which being hereby incorporated by reference.

FIELD

The disclosure relates to a surgical apparatus for use in minimally invasive surgical procedures, such as endoscopic and/or laparoscopic procedures and, more particularly, to three-prong laparoscopic grasping devices.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy, and laryngobronchoscopy, just to name a few. In these procedures, trocars are utilized for creating incisions through which the endoscopic surgery is performed. Trocar tubes or cannula assemblies are extended into and left in place in the abdominal wall to provide access for endoscopic surgical tools. A camera or scope is inserted through a cannula assembly to permit the visual inspection and magnification of the body cavity. The surgeon can then perform diagnostic and/or therapeutic procedures at the surgical site with the aid of specialized instrumentation, such as forceps, graspers, cutters, applicators, and the like, which are designed to fit through additional cannulas.

Graspers configured for use in laparoscopic procedures generally have two prongs. Tissue manipulation with two-prong graspers is limited as the opposed prongs of the two-prong graspers provide minimal security and purchase on tissue.

SUMMARY

A three-prong grasper for laparoscopic procedures includes an elongate body defining a longitudinal axis and including a sleeve having a distal portion, and an end effector supported on the distal portion of the sleeve. The end effector includes a first prong assembly having a first base member and a first prong member pivotally secured to the first base member, a second prong assembly having a second base member and a second prong member pivotally secured to the second base member, and a third prong assembly having a third base member and a third prong member pivotally secured to the third base member. The first, second, and third prong members are movable between an open configuration and a closed configuration.

In certain aspects of the disclosure, the laparoscopic grasper includes a handle assembly. The handle assembly may include a trigger and retraction of the trigger moves the end effector to the open position. The handle assembly may include a trigger and retraction of the trigger may move the end effector to the closed position. Each of the first, second, and third prong members may include a body portion. The body portions of the first, second, and third prong members may extend parallel to the longitudinal axis of the elongate body when the end effector is in the closed configuration. The laparoscopic grasper may include an attachment portion on a first end of each of the body portions and an engagement portion on a second end of each of the body portions. Each of the engagement portions may form a tenaculum. The laparoscopic grasper may include a drive shaft in operable engagement with the first, second, and third prong members. Each of the first, second, and third prong members may pivot individually relative to the respective first, second, and third members.

A laparoscopic grasper includes an elongate body defining a longitudinal axis and including a sleeve having a distal portion, a drive shaft extending through the sleeve and having a distal portion, and an end effector supported on the distal portion of the sleeve and in operable engagement with the drive shaft. The end effector includes a first prong assembly having a first prong member pivotally secured to a first link member, and the first link member pivotally secured to the distal portion of the drive shaft, a second prong assembly having a second prong member pivotally secured to a second link member, and the second link member pivotally secured to the distal portion of the drive shaft, and a third prong assembly having a third prong member pivotally secured to a third link member, and the third link member pivotally secured to the distal portion of the drive shaft. The first, second, and third prong members are movable between an open configuration and a closed configuration.

A method of grasping tissue includes positioning tissue to be grasped between first, second, and third prong members of a grasping device, and retracting a drive shaft to cause pivoting of each of the first, second, and third prong members of the grasping device relative to a sleeve of the grasping device to move the first, second, and third prong members to a closed position.

In certain aspects of the disclosure, the method includes advancing the drive shaft to cause the pivoting of each of the first, second, and third prong members of the grasping device relative to the sleeve of the grasping device to move the first, second, and third prong members to an open position. The method may further include receiving the first, second, and third prong members of the grasping device through an access assembly.

BRIEF DESCRIPTION OF THE DRAWINGS

Various aspects of the disclosed systems and methods are described herein below with reference to the drawings, wherein:

FIG. 10 is a cross-sectional side view of a prong assembly according to another aspect of the disclosure, in a closed position;

FIG. 11 is a cross-sectional side view of the prong assembly shown in FIG. 10 in an open position.

DETAILED DESCRIPTION

Figure 1:
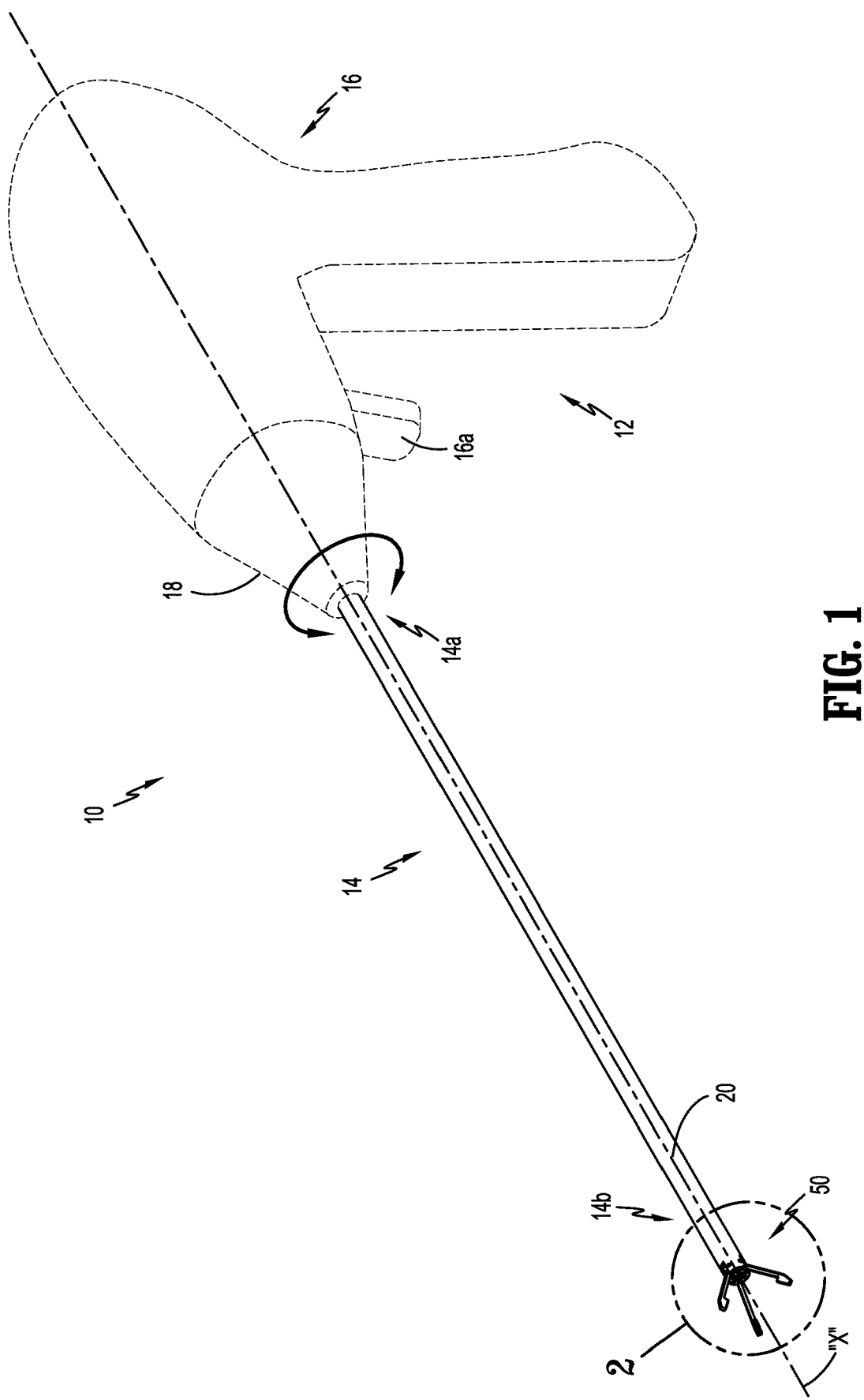
FIG. 1 is a perspective view of a laparoscopic grasper according to an aspect of the disclosure, with a handle assembly shown in phantom and an end effector in an open configuration.

The three-prong laparoscopic graspers are described in detail with reference to the drawings, in which like reference numerals designate identical or corresponding elements in each of the several views. As used herein the term "distal" refers to that portion of the trocar, or component thereof, farther from the user, while the term "proximal" refers to that portion of the trocar, or component thereof, closer to the user. In addition, the term "laparoscopic" or "laparoscope" is used generally used to refer to minimally invasive procedures such as endoscopic, laparoscopic, arthroscopic, and/or any other procedure conducted through small diameter incision or cannula. Further, the term "clinician" is used generally to refer to medical personnel including doctors, nurses, and support personnel.

Disclosed are three-prong graspers configured for use in laparoscopic procedures. The three-prong graspers are sized to be received into a body cavity of a patient through an incision, with or without the aid of an access assembly. The three-prong graspers offer greater surface area contact on a tissue specimen over traditional two-prong graspers and may be more atraumatic. Instead of clamping tissue, as with traditional two-prong graspers, the three-prong graspers surround tissue to provide greater security and purchase on a tissue specimen.

FIG. 1 illustrates a three-prong grasper according to an aspect of the disclosure, shown generally as grasper 10. The grasper 10 includes a handle assembly 12, an elongate body 14 extending from the handle assembly 12, and an end effector 50 operably disposed on a distal portion 14b of the elongate body 14.

As shown, the handle assembly 12 of grasper 10 includes a fixed handle 16. In certain aspects of the disclosure, the handle assembly 12 includes a robotic system or other automated system. The fixed handle 16 may include a pistol grip, as shown, including a trigger 16a, or a pencil grip. It is envisioned that the handle 16 may be configured such that pulling the trigger 16a towards the handle 16 closes the end effector 50. Alternatively, the fixed handle 16 may be configured such that pulling the trigger 16a towards the fixed handle 16 opens the end effector 50. The fixed handle 16 may be manually actuated, motorized, or a combination thereof.

It is envisioned that the handle assembly 12 of the grasper 10 may be configured to close the first, second, and third prong assemblies 100, 200, 300 to apply a predetermined force to tissue captured therebetween, to a predetermined tissue gap between the first, second, and third prong members 102, 202, 302, and/or the tension may be adjusted by the user, either manually or automatically. In this manner, a user may modify the closer characteristics of the grasper 10 based on the tissue being manipulated.

The distal portion 14b of the elongate body 14 and end effector 50 of the grasper 10 are configured to be received through an access port (not shown) or other access assembly. It is envisioned that the distal portion 14b elongate body 14 of the grasper 10 may include one or more articulation joints (not shown) for permitting articulation of the end effector 50 relative to the longitudinal axis. It is envisioned that the end effector 50 may be releasably connected to the elongate body 14, e.g., as a loading unit. Alternatively, or in addition, the elongate body 14 may be configured for releasable connection with handle assembly 12.

The elongate body 14 of the grasper 10 may include a rotation knob 18 for rotating the end effector 50 about a longitudinal axis "x" of the elongate body 14. A sleeve 20 extends from the rotation knob 18. As will be described in further detail below, a drive shaft 30 operably engages the handle assembly 12 to facilitate actuation of the end effector 50.

Figure 2:
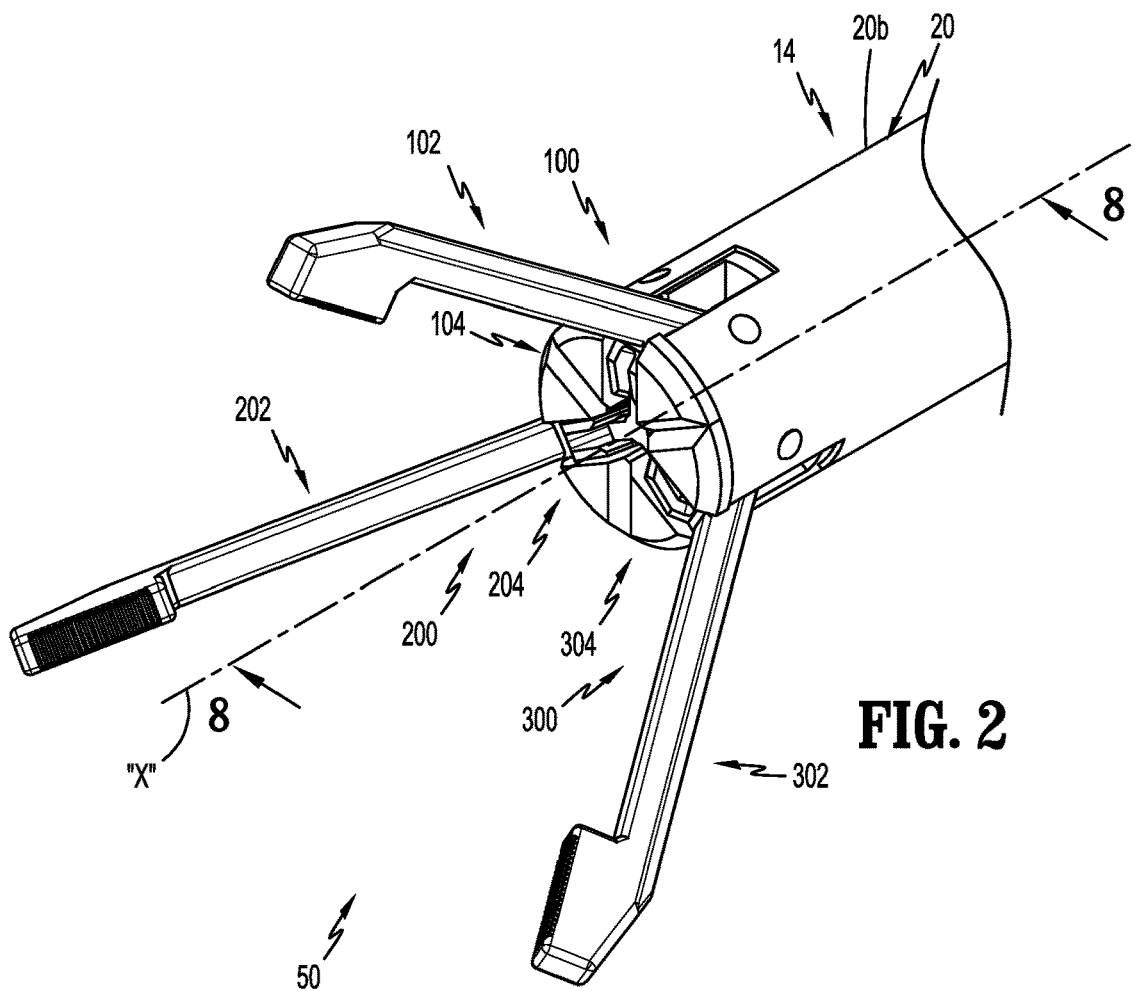
FIG. 2 is an enlarged view of the indicated area of detail shown in FIG. 1.

FIG. 2 illustrates the end effector 50 of the grasper 10 (FIG. 1) in an open configuration. The end effector 50 is operably coupled to a distal end 20b of the sleeve 20 of elongate body 14. The end effector 50 includes first, second and third prong assemblies 100, 200, 300. Each of the first, second, and third prong assemblies 100, 200, 300 includes a prong member 102, 202, 302, and a base member 104, 204, 304 (FIG. 4) for pivotally securing the respective first, second, and third prong members 102, 202, 302 to the distal end 20b of the sleeve 20. When the end effector 50 is in the open configuration, the first, second, and third prong members 102, 202, 302 of the respective first, second, and third prong assemblies 100, 200, 300 are configured to be positioned about tissue.

Figure 3:
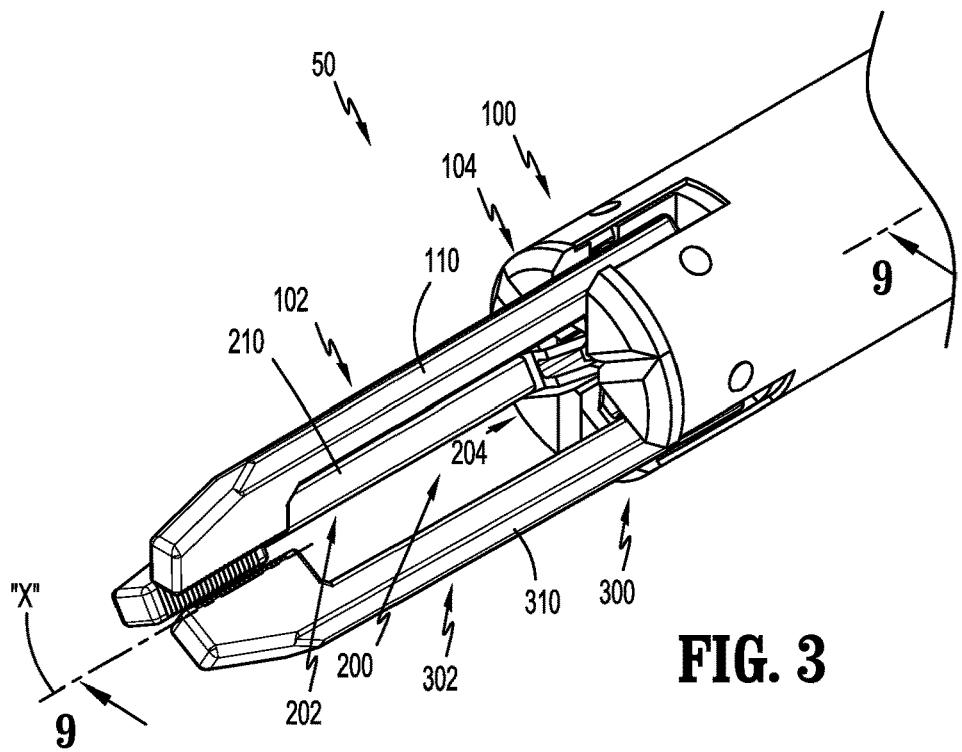
FIG. 3 is the enlarged view shown in FIG. 2, with the end effector in a closed configuration.

FIG. 3 illustrates the end effector 50 of the grasper 10 (FIG. 1) in a closed configuration. It is envisioned that, in addition to being moved to the closed configuration to grasp tissue, the end effector 50 is moved to the closed configuration to facilitate insertion of the end effector 50 through an access port (not shown). In the closed position, the first, second, and third prong assemblies 100, 200, 300 are maintained within an outer diameter of the distal end 20b of the sleeve 20.

Figure 4:
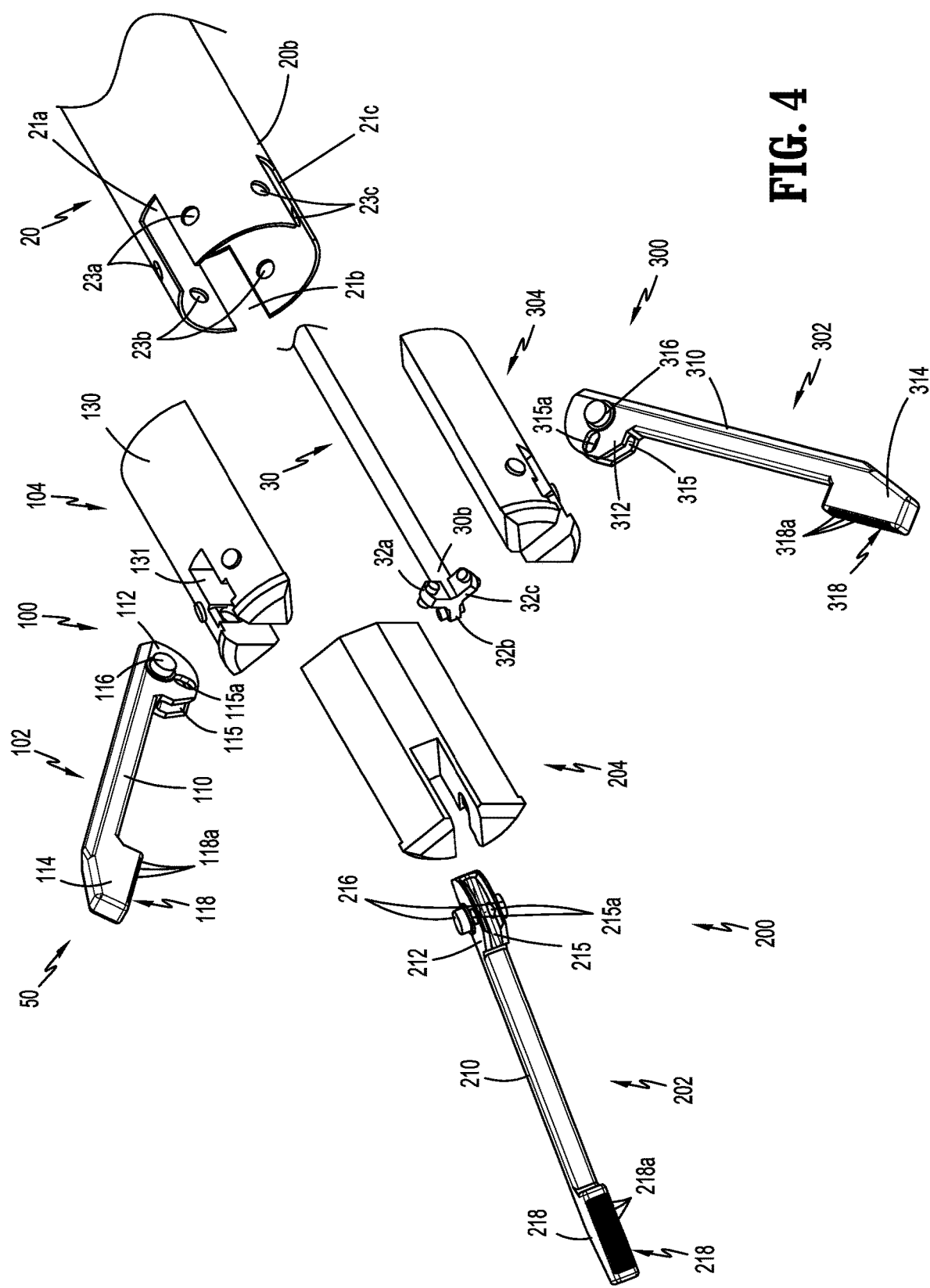
FIG. 4 is an exploded perspective view of a distal end of the grasper shown in FIG. 1, with parts separated.

FIG. 4 illustrates an exploded view of the end effector 50 of the grasper 10 (FIG. 1). As noted above, the end effector 50 includes the first, second, and third prong assemblies 100, 200, 300. The first, second, and third body portions 110, 210, 310 of the respective first, second, and third prong assemblies 100, 200, 300 are pivotally secured to respective base members 104, 204, 304 and are supported in the distal end 20b of sleeve 20 of the elongate body 14 of the grasper 10.

The distal end 20b of the sleeve 20 defines first, second, and third slots 21a, 21b, 21c for accommodating respective first, second, and third prong members 102, 202, 302 of the respective first, second, and third prong assemblies 100, 200, 300. Openings 23a, 23b, 23c are formed on either side of the respective first, second, and third slots 21a, 21b, 21c and are configured to receive locking tabs of the respective first, second, and third base members 104, 204, 304 of the respective first, second, and third prong assemblies 100, 200, 300.

The drive shaft 30 of the grasper 10 extends through the sleeve 20 of the elongate body 14. As will be described in further detail below, the drive shaft 30 includes a distal end 30b configured for operable engagement with the first, second, and third prong assemblies 100, 200, 300 of the end effector 50.

Each of the first, second, and third prong members 102, 202, 302 of the respective first, second, and third prong assemblies 100, 200, 300 includes attachment portions 112, 212, 312, respectively, engagement portions 114, 214, 314, respectively, disposed on a proximal end of the respective attachment portions 112, 212, 312, and pivot members 116, 216, 316, respectively, disposed on a distal end of the respective attachment portions 112, 212, 312. As shown, each of the first, second, and third prong members 102, 202, 302 is substantially similar. It is envisioned that any or all of the prong members 102, 202, 302 may be different.

The body portions 110, 210, 310 of the respective first, second, and third prong assemblies 100, 200, 300 of the end effector 50 extends between the respective attachment portions 112, 212, 312 of the respective first, second, and third prong members 102, 202, 302 and the respective engagement portions 114, 214, 314 of the respective first, second, and third prong members 102, 202, 302. The body portions 110, 210, 310 of the respective first, second, and third prong assemblies 100, 200, 300 may be of any length, and include a cross-section of any configuration, e.g., a rectangular cross-section, as shown.

The body portions 110, 210, 310 of the respective first, second, and third prong members 102, 202, 302 of the respective first, second, and third prong assemblies 100, 200, 300 may extend parallel to the longitudinal axis "x" of the elongate body 14 when the end effector 50 is in the closed configuration (FIG. 3). The body portions 110, 210, 310 of the respective first, second, and third prong members 102, 202, 302 extend radially outward from the longitudinal axis "x" when the end effector 50 is in the open configuration (FIG. 2). It is envisioned that the first, second, and third prong members 102, 202, 302 of the respective first, second, and third prong assemblies 100, 200, 300 may be configured to open to a position that is perpendicular to the longitudinal axis "x".

Each attachment portion 112, 212, 312 of the respective first, second, and third prong members 102, 202, 302 of the respective first, second, and third prong assemblies 100, 200, 300 includes a pair of pivot members 116, 216, 316, and defines a channel 115, 215, 315 with openings 115a, 215a, 315a on either side of the respective channels 115, 215, 315. The pivot members 116, 216, 316 are configured to pivotally secure the respective first, second, and third prong members 102, 202, 302 to the respective base members 104, 204, 304 of the respective first, second, and third prong assemblies 100, 200, 300. The channels 115, 215, 315 are configured to receive respective first, second, and third flanges 32a, 32b, 32c on the distal end 30b of the drive shaft 30. The openings 115a, 215a, 315a are configured to receive the pivot members 34a, 34b, 34c (FIG. 7) formed on the respective first, second, and third flanges 32a, 32b, 32c of the drive shaft 30. The openings 115a, 215a, 315a are substantially oval in shape to accommodate the pivoting of the respective first, second, and third prong members 102, 202, 302 relative to the drive shaft 30.

Each engagement portion 114, 214, 314 of the respective first, second, and third prong members 102, 202, 302 of the respective first, second, and third prong assemblies 100, 200, 300 includes tissue contacting surfaces 118, 218, 318, respectively. The tissue contacting surfaces 118, 218, 318 may all be substantially similar, two of the tissue contacting surfaces 118, 218, 318 may be the same, or all three tissue contacting surfaces 118, 218, 318 may be different. As shown, the tissue contacting surfaces 118, 218, 318 of the respective engagement portions 114, 214, 314 are planar and include ridges 118a, 218a, 318a. It is envisioned that the tissue contacting surfaces 118, 218, 318 may include a tenaculum (FIG. 10; 418) or be otherwise configured for engaging tissue. The tissue contacting surfaces 118, 218, 318 may extend parallel to each other and the longitudinal axis "x" when the end effector 50 is in the closed configuration as shown in FIG. 2 and may be spaced apart from each other, as shown in FIG. 3. Alternatively, the tissue contacting surfaces 118, 218, 318 may engage one another, and/or may define an angle relative to longitudinal axis "x".

Figure 5:
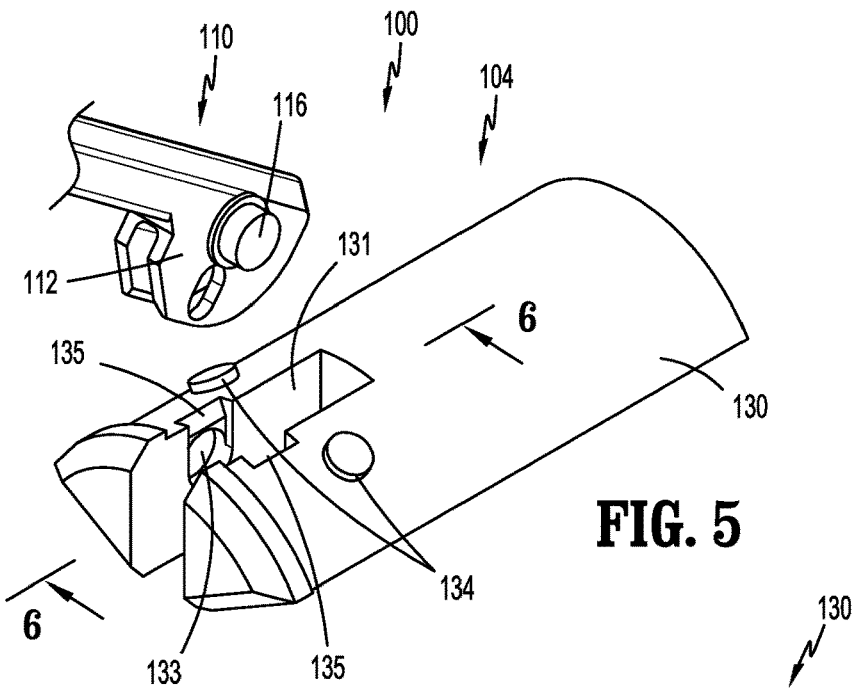
FIG. 5 is an enlarged view of a base member and an attachment portion of a prong member of a prong assembly of the end effector of the grasper shown in FIG. 1.

FIG. 5 illustrates the base member 104 of the first prong assembly 100 of the end effector 50. The end effector 50 will be described in detail with respect to base member 104. The base members 204, 304 of the second and third prong assemblies 200, 300 are substantially similar to the base member 104 of the first prong assembly 100. It is to be understood that any feature described as it relates to the base member 104 may be equally applicable to either or both of the other base members 204, 304. It is envisioned that, in aspects of the disclosure, the individual base members 104, 204, 304 may be replaced by a single base member (not shown).

The base member 104 of the first prong assembly 100 includes a substantially wedge-shaped body 130 defining a slot 131 for receiving the attachment portion 112 of the first prong member 102. The slot 131 in the base member 104 aligns with the slot 21a (FIG. 4) in the distal end 20b of the sleeve 20. The body 130 of the base member 104 further defines a pair of openings 133 (only one shown) in communication with the slot 131 for receiving the pivot members 116 extending from the attachment portion 112 of the first prong member 102. The body 130 of the base member 104 further defines a pair of cutouts 135 aligned with the openings 133 to facilitate receipt of the pivot members 116 of the attachment portion 112 of the first prong member 102 within the openings 133.

A locking tab 134 extends from the body 130 of the base member 104 on either side of the slot 131. The locking tabs 134 are receivable within the openings 23a formed on either side of the slot 21a in the distal end 20b of the sleeve 20. Receipt of the locking tabs 134 within the openings 23a secure the first prong assembly 100 relative to the sleeve 20. Although shown with locking tabs 134 and openings 23a, it is envisioned that first prong assembly 100 may be secured to the sleeve 20 in any suitable manner, including, for example, with adhesive, friction fit, mechanical fasteners, and/or welding.

Figure 7:
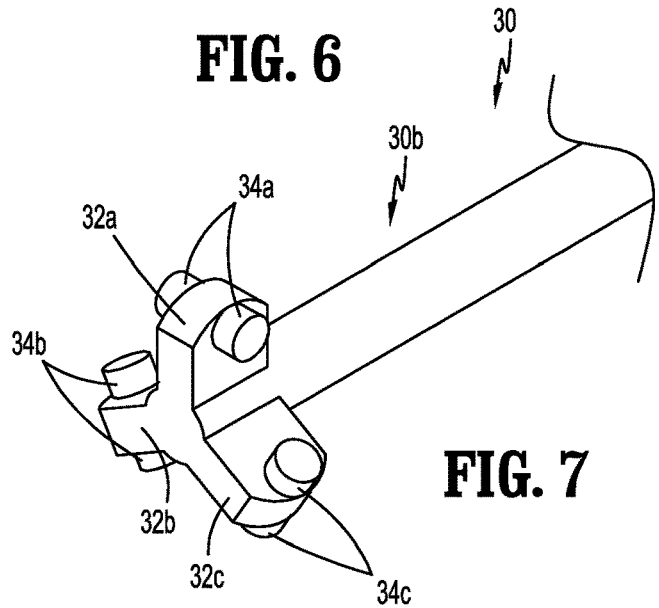
FIG. 7 is an enlarged perspective view of a distal end of a drive shaft of the grasper shown in FIG. 1.

FIG. 7 illustrates the distal end 30b of the drive shaft 30 of the grasper 10 including first, second, and third flanges 32a, 32b, 32c extending radially outward. Each of first, second, and third flanges 32a, 32b, 32c includes pivot members 34a, 34b, 34c, respectively. The pivot members 34a, 34b, 34c are receivable within respective openings 115a, 215a, 315a in the attachment portions 112, 212, 312, respectively, of the respective first, second, and third prong members 102, 202, 302 when the respective first, second, and third flanges 32a, 32b, 32c of the drive shaft 30 are received within the respective channels 115, 215, 315 of the respective first, second, and third prong members 102, 202, 302.

It is envisioned that the drive shaft 30 may be separated into two or three independent drive shafts (not shown). The independent drive shafts are configured to individually actuate each of the first, second, and third prong members 102, 202, 302. In this manner, one or two of the first, second, and third prong members 102, 202, 302 may be moved while the other of the first, second, and third prong members 102, 202, 302 are stationary.

The operation of the end effector 50 will be described as relates to first prong assembly 100. It is understood that the second and third prong assemblies 200, 300 (FIG. 4) operate in a substantially similar manner.

Figure 6:
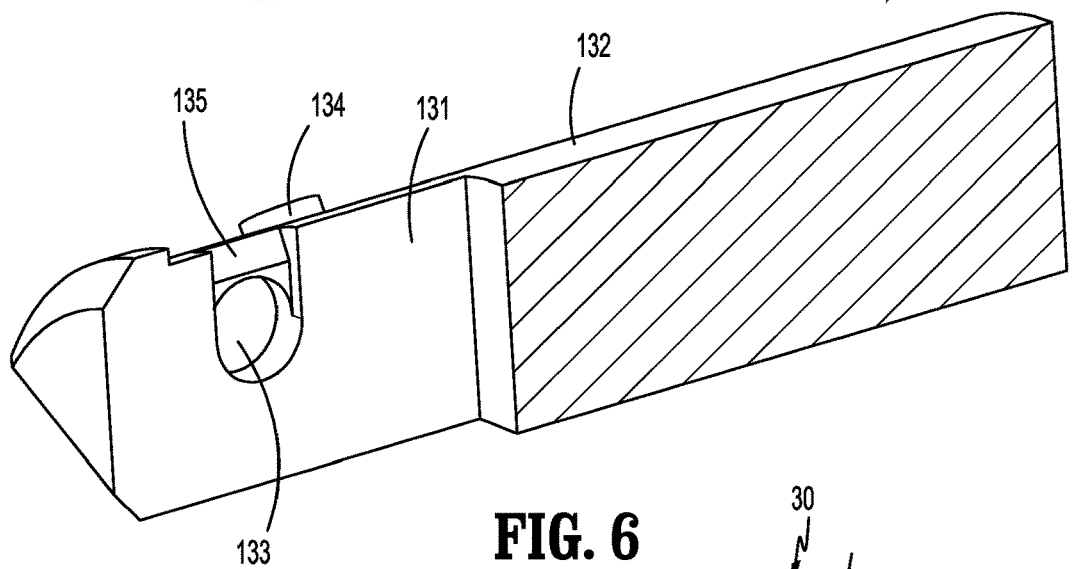
FIG. 6 is a side cross-sectional view taken along section line 6-6 in FIG. 5.
Figure 8:
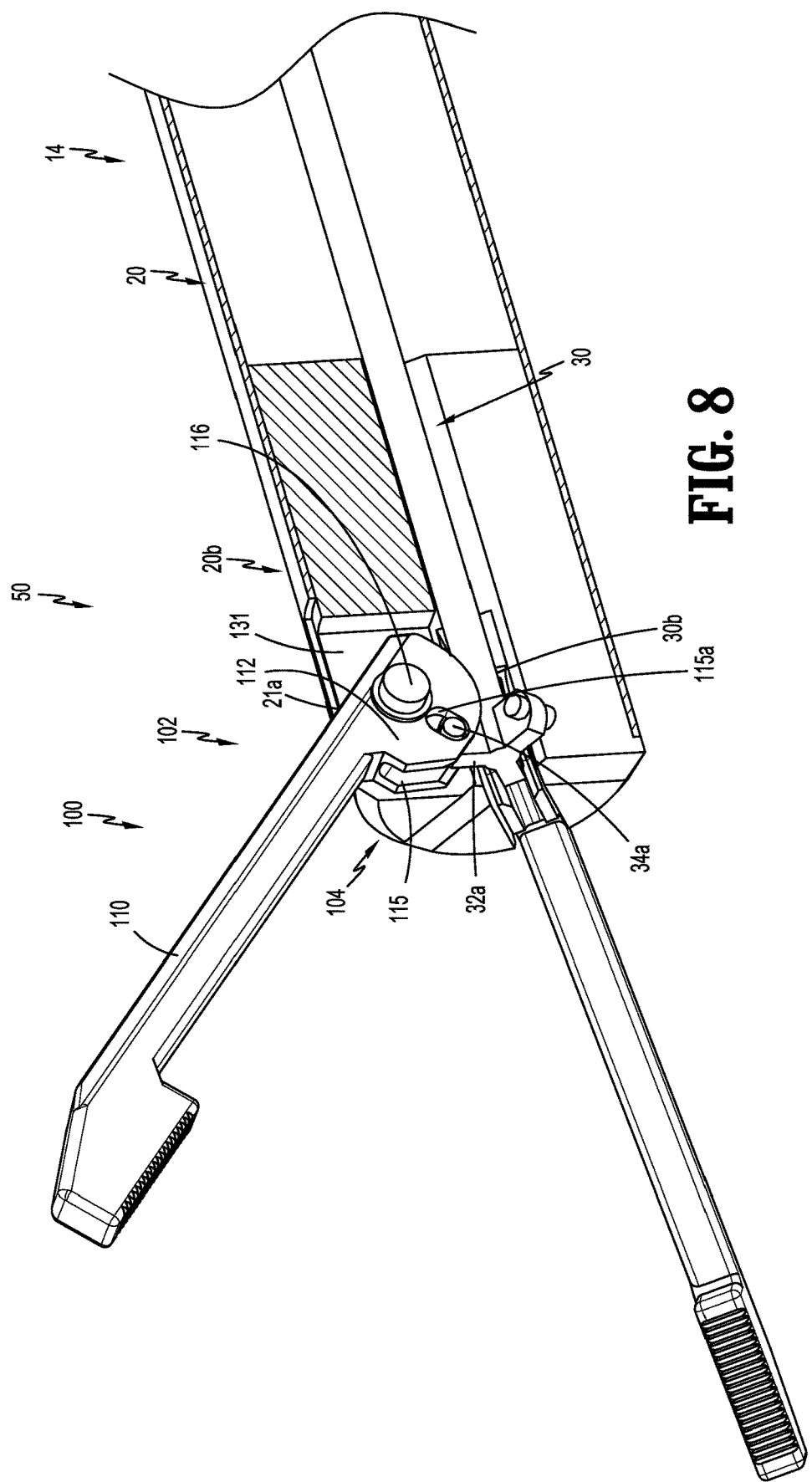
FIG. 8 is a side cross-sectional view the distal end of the grasper shown in FIG. 2 taken along section line 8-8 in FIG. 2.

FIG. 8 illustrates a cross-sectional view of the end effector 50 of the grasper 10 in the open configuration. The first prong member 102 of the first prong assembly 100 is received through the slot 23a formed in the distal end 20b of sleeve 20 and within the slot 131 formed in the base member 104 of the first prong assembly 100 such that the pivot members 116 extending from the attachment portion 112 of the first prong member 102 are received within openings 133 (FIG. 6) in the base member 104. In this manner, the first prong member 102 is pivotable relative to the base member 104 between the open position, as shown, and the closed position shown in FIG. 9.

The first prong member 102 is movable between the open and closed positions through engagement with the drive shaft 30. The distal end 30b of the drive shaft 30 is in operable engagement with the first prong assembly 100. More particularly, the first flange 32a of the distal end 30b of the drive shaft 30 is received within the channel 115 in the attachment portion 112 of the first prong member 102 of the first prong assembly 100 such that the pivot members 34a extending from the first flange 32a are received within the openings 115a in the attachment portion 112. In this manner, the first prong member 102 of the first prong assembly 100 is configured to pivot relative to the drive shaft 30.

Figure 9:
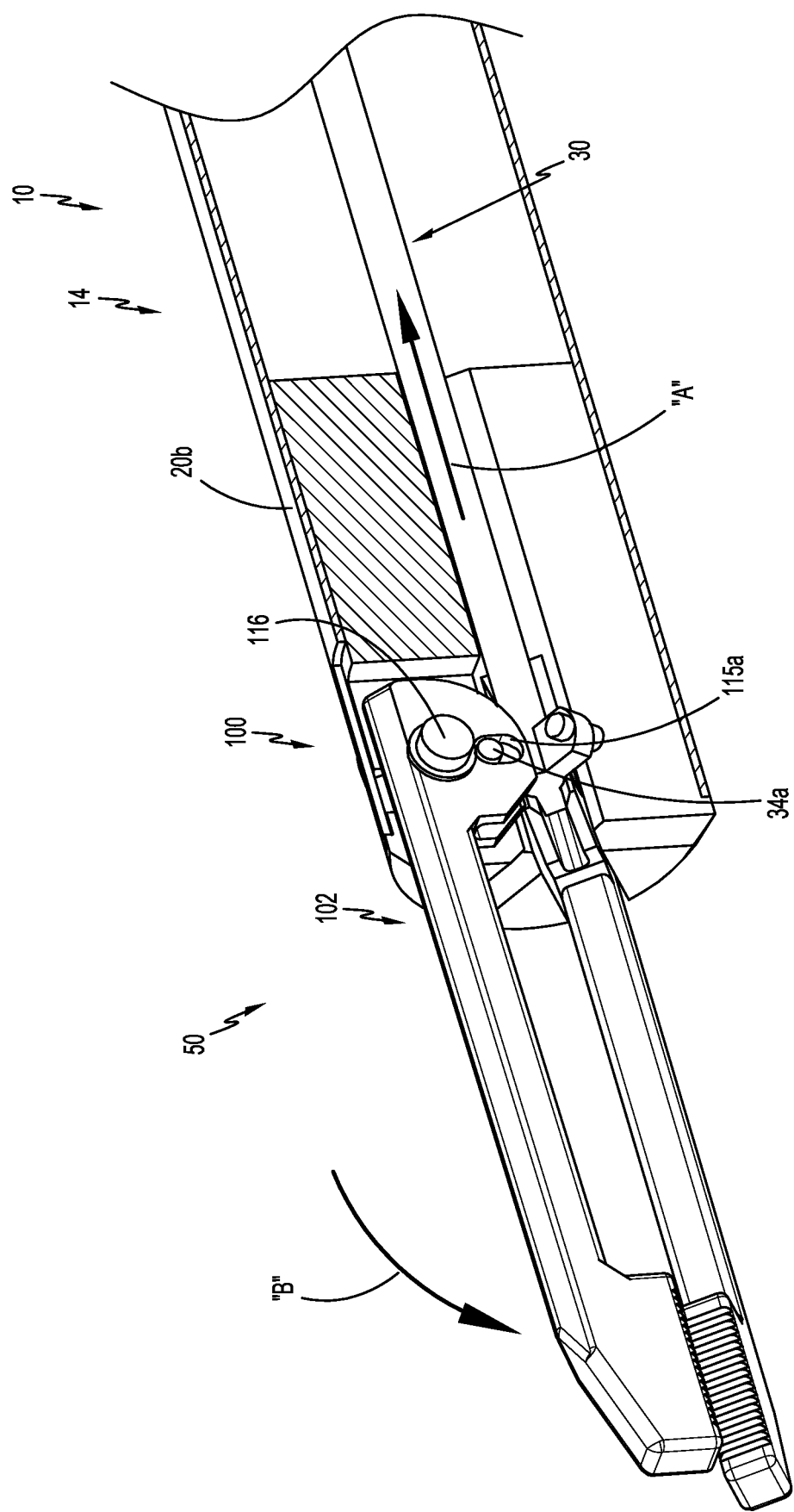
FIG. 9 is a side cross-sectional view the distal end of the grasper shown in FIG. 3 taken along section line 9-9 in FIG. 3.

FIG. 9 illustrates a cross-sectional view of the end effector 50 of the grasper 10 in the closed configuration. Retraction of the drive shaft 30, as indicated by arrow "A", causes the first prong member 102 to pivot about pivot members 116, as indicated by arrow "B", to the closed position. More particularly, as the drive shaft 30 is retracted, engagement of the pivot member 34a of the of the first flange 32a of the drive shaft 30 with the attachment portion 112 of the first prong member 102 pivots the first prong member 102 about pivot members 116 of the first prong member 102. As noted above, the oval shape of the openings 115a accommodates the pivoting of the first prong member 102 about pivot members 116.

The end effector 50 of the grasper 10 may be returned to the open position through advancement of the drive shaft 30. More particularly, as the drive shaft 30 is advanced, engagement of the pivot member 34a of the of the first flange 32a of the drive shaft 30 with the attachment portion 112 of the first prong member 102 pivots the first prong member 102 about pivot members 116 of the first prong member 102.

FIGS. 10 and 11 illustrate a prong assembly according to another aspect of the disclosure shown generally as prong assembly 400. The prong assembly 400 includes a prong member 402 and a link member 404. The prong assembly 400 may further include a base member (not shown). The prong member 402 is pivotally secured relative to the sleeve 20' at pivot point 416a. The linkage member 404 includes a first end pivotally secured to the prong member 402 at a second pivot point 416b and a second end pivotally secured to a drive shaft 30' at third pivot point 416c.

The prong assembly 400 is configured such that when the drive shaft 30' is advanced, as indicated by arrow "C" in FIG. 11, the prong member 402 pivots relative to the sleeve 20' from an open position (FIG. 11) to a closed position (FIG. 10), as indicated by arrow "D" in FIG. 11. More particularly, as the drive shaft 30' is advanced, the link member 404 pivots relative to the drive shaft 30', as indicated by arrow "E" in FIG. 11, which causes the first end of the linkage member 404 to move laterally or radially outward relative to the drive shaft 30', as indicated by arrow "F" in FIG. 11. Because the link member 404 is connected to the prong member 402 at the second pivot point 416b, the radial outward movement of the first end of the linkage member 404 causes corresponding lateral or radially outward movement of a first end of the prong member 402 relative to the drive shaft 30'. Outward movement of the first end of the prong member 402 results in the pivoting of the prong member about pivot point 416a, as indicated by arrow "D" in FIG. 11, to the open position.

Retraction of the drive shaft 30' pivots the prong member 402 to the closed position (FIG. 10). More particularly, as the drive shaft 30' is retracted, the link member 404 pivots relative to the drive shaft 30' which causes the first end of the linkage member 404 to move laterally or radially inward relative to the drive shaft 30'. The radial inward movement of the first end of the linkage member 404 causes corresponding lateral or radially inward movement of a first end of the prong member 402 relative to the drive shaft 30'. Inward movement of the first end of the prong member 402 results in the pivoting of the prong member about pivot point 416a to the closed position.

Any of the components described herein may be fabricated from either metals, plastics, resins, composites or the like taking into consideration strength, durability, wearability, weight, resistance to corrosion, ease of manufacturing, cost of manufacturing, and the like. In aspects, the elongate body of the cannula assembly may be made of metals, such as stainless steel, while the seals may be formed of an elastomeric plastic or rubber.

Figure 12:
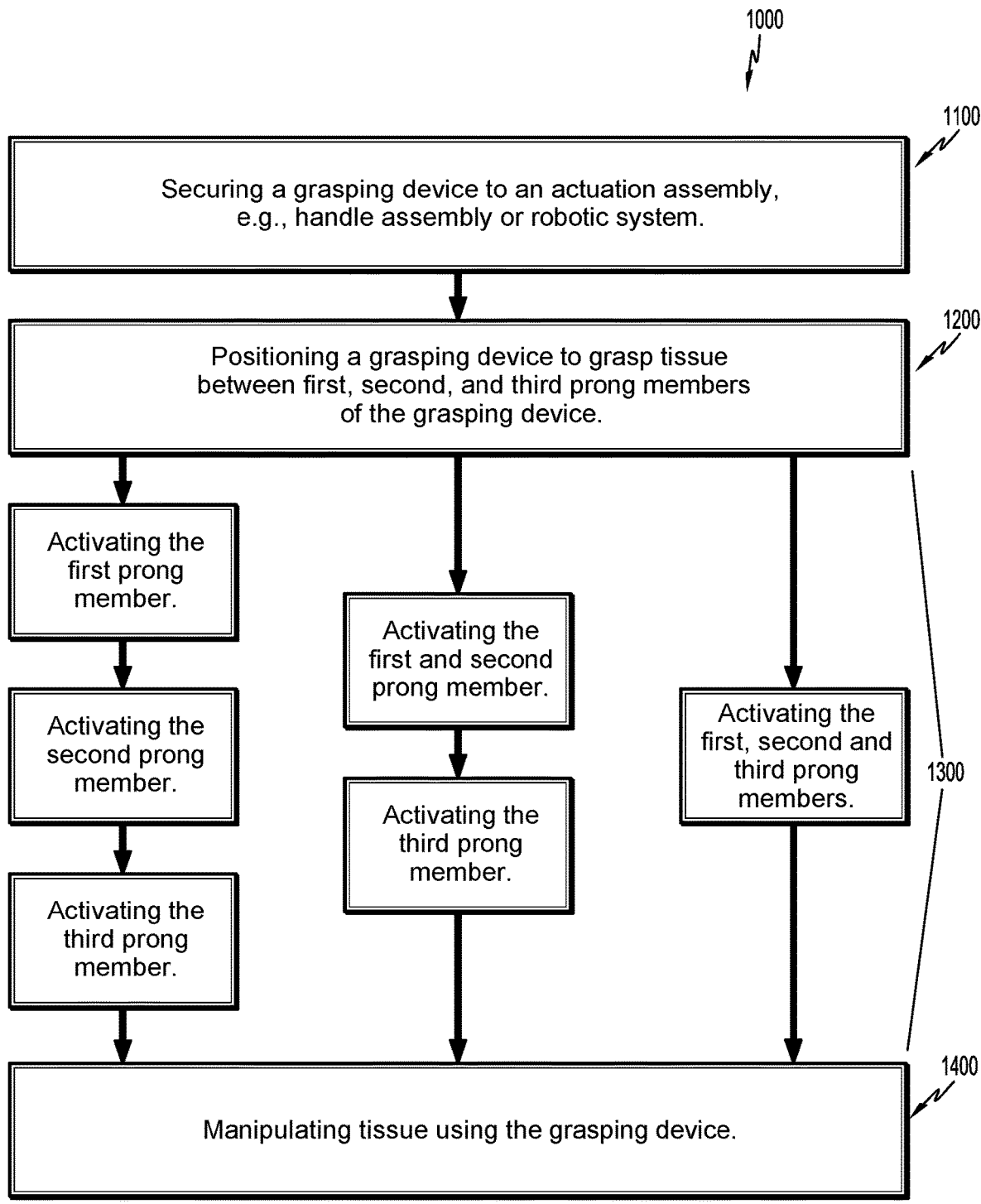
FIG. 12 is a flow chart of the method of grasping tissue of the disclosure.

FIG. 12 illustrates a flow diagram of a method of grasping tissue according to aspects of the disclosure, shown generally as method 1000. If the grasping end effector 50 is not already provided to the clinician secured to the actuation assembly, e.g., handle assembly 12 (FIG. 1) or a robotic system (not shown), the grasping end effector 50 is secured to the actuation assembly during an assembly step 1100. Attachment of the end effector 50 to the actuation assembly may be with bayonet coupling, mechanical fasteners or the like. In aspects of the disclosure, it is envisioned that the end effector 50 is provided preassembled with handle assembly 12.

Once secured to the actuation assembly, the clinician may then position the end effector 50 about tissue to be grasped during a positioning step 1200. Positioning of the end effector 50 may occur manually or using an automated system, e.g., robotics. Positioning of the end effector 50 may be accomplished in an open procedure, or through a port or other access assembly.

Once the end effector 50 is positioned in a desired location relative to tissue, one, two or all of the first, second, and third prong assemblies 100, 200, 300 may be activated to cause the pivoting of the respective first, second, and third prong members 102, 202, 302 relative to the respective base members 104, 204, 304 to grasp and/or manipulate tissue during a grasping step 1300. Each of the first, second, and third prong assemblies 100, 200, 300 may then continue to be activated individually and/or simultaneously to permit the grasping and manipulating of tissue as necessary throughout a surgical procedure, during a manipulating step 1400.

It will be understood that various modifications may be made to the disclosed methods and systems. Therefore, the above description should not be construed as limiting, but merely as exemplifications of aspects of the disclosure. Those skilled in the art will envision other modifications within the scope and spirit of the disclosure. For example, any and all features of one described aspect may be suitably incorporated into another aspect.

What is claimed is:

1. A laparoscopic grasper comprising:
    an elongate body defining a longitudinal axis and including a sleeve having a distal portion;
    a drive shaft disposed in the sleeve, the drive shaft axially repositionable between a first position and a second position;
    a plurality of protrusions disposed on a distal end portion of the drive shaft; and
    an end effector supported on the distal portion of the sleeve, the end effector including:
        a first prong assembly having a first base member and a first prong member pivotally secured to the first base member, the first prong member including a first opening for rotatably receiving a first protrusion of the plurality of protrusions;
        a second prong assembly having a second base member and a second prong member pivotally secured to the second base member, the second prong member including a second opening for rotatably receiving a second protrusion of the plurality of protrusions; and
        a third prong assembly having a third base member and a third prong member pivotally secured to the third base member, the third prong member including a third opening for rotatably receiving a third protrusion of the plurality of protrusions, wherein the first prong member, the second prong member, and the third prong member are movable between an open configuration when the drive shaft is in the first position and a closed configuration when the drive shaft is in the second position.

2. The laparoscopic grasper of claim 1, further including a handle assembly.

3. The laparoscopic grasper of claim 1, wherein each of the first prong member, the second prong member, and the third prong member includes a body portion.

4. The laparoscopic grasper of claim 3, wherein the body portions of the first prong member, the second prong member, and the third prong member extend parallel to the longitudinal axis of the elongate body when the first prong member, the second prong member, and the third prong member are in the closed configuration.

5. The laparoscopic grasper of claim 3, further including an attachment portion on a first end of each of the body portions.

6. The laparoscopic grasper of claim 5, further including an engagement portion on a second end of each of the body portions.

7. The laparoscopic grasper of claim 6, wherein each of the engagement portions forms a tenaculum.

8. The laparoscopic grasper of claim 2, wherein the handle assembly includes a trigger and retraction of the trigger moves the first prong member, the second prong member, and the third prong member to the closed configuration.

9. The laparoscopic grasper of claim 2, wherein the handle assembly includes a trigger and retraction of the trigger moves the first prong member, the second prong member, and the third prong member to the open configuration.

10. The laparoscopic grasper of claim 1, wherein each of the first prong member, the second prong member, and the third prong member is pivoted individually.

* * * * *